United States Patent [19]

Rabin et al.

[11] Patent Number: 5,569,365

[45] Date of Patent: Oct. 29, 1996

[54] INTERMITTENT ELECTROLYTIC MEMBRANE SUPPRESSOR REGENERATION FOR ION CHROMATOGRAPHY

[75] Inventors: Steven B. Rabin, Mountain View, Calif.; Hamish Small, Leland, Mich.; John M. Riviello, Santa Cruz, Calif.

[73] Assignee: Dionex Corporation, Sunnyvale, Calif.

[21] Appl. No.: 398,147

[22] Filed: Mar. 3, 1995

[51] Int. Cl.$^6$ .............................. B01D 15/08; B01D 61/48
[52] U.S. Cl. .......................... 204/450; 204/520; 204/536; 204/542; 210/635; 210/638; 210/656; 210/659; 210/662; 210/663
[58] Field of Search ...................... 204/450, 520, 204/536, 542; 210/635, 638, 656, 659, 662, 663

[56] References Cited

U.S. PATENT DOCUMENTS

| | | | |
|---|---|---|---|
| 3,920,397 | 11/1975 | Small | 23/230 R |
| 4,403,039 | 9/1983 | Ban | 436/150 |
| 4,459,357 | 7/1984 | Jansen | 436/161 |
| 4,999,098 | 3/1991 | Pohl | 204/301 |
| 5,248,426 | 9/1993 | Stillian | 210/635 |
| 5,352,360 | 10/1994 | Stillian | 210/198.2 |
| 5,433,838 | 7/1995 | Dasgupta et al. | 204/299 R |

FOREIGN PATENT DOCUMENTS 59-133459  7/1984  Japan.

OTHER PUBLICATIONS

Rabin et al., J. Chromatog 640 (1993) pp. 97–109, "New membrane-based electrolytic suppressor device for suppressed conductivity detection in ion chromatography".

Tian et al., J. Chromatog 439 (1988) pp. 159–163 "High performance electrochemical suppressor for ion chromatography".

Small, H., Ion Chromatography, Plenum Press (1989) pp. 164–167.

*Primary Examiner*—Arun S. Phasge
*Attorney, Agent, or Firm*—Flehr, Hohbach, Test, Albritton & Herbert

[57] ABSTRACT

A method and apparatus using suppression of eluents for the analysis of anions or cations in ion chromatography. The invention relates to the intermittent use of the electric field during electrochemical suppression to minimize background noise during detection of the ionic species caused by the application of an electric field using an electrolytic membrane suppressor. Using this intermittent electrochemical suppression system allows the detection of the analyte in the absence of the electric field. The system finds particular benefit in reducing background noise created during electrochemical suppression, and in reducing the baseline interference when analyzing organic solvent-containing samples.

8 Claims, 8 Drawing Sheets

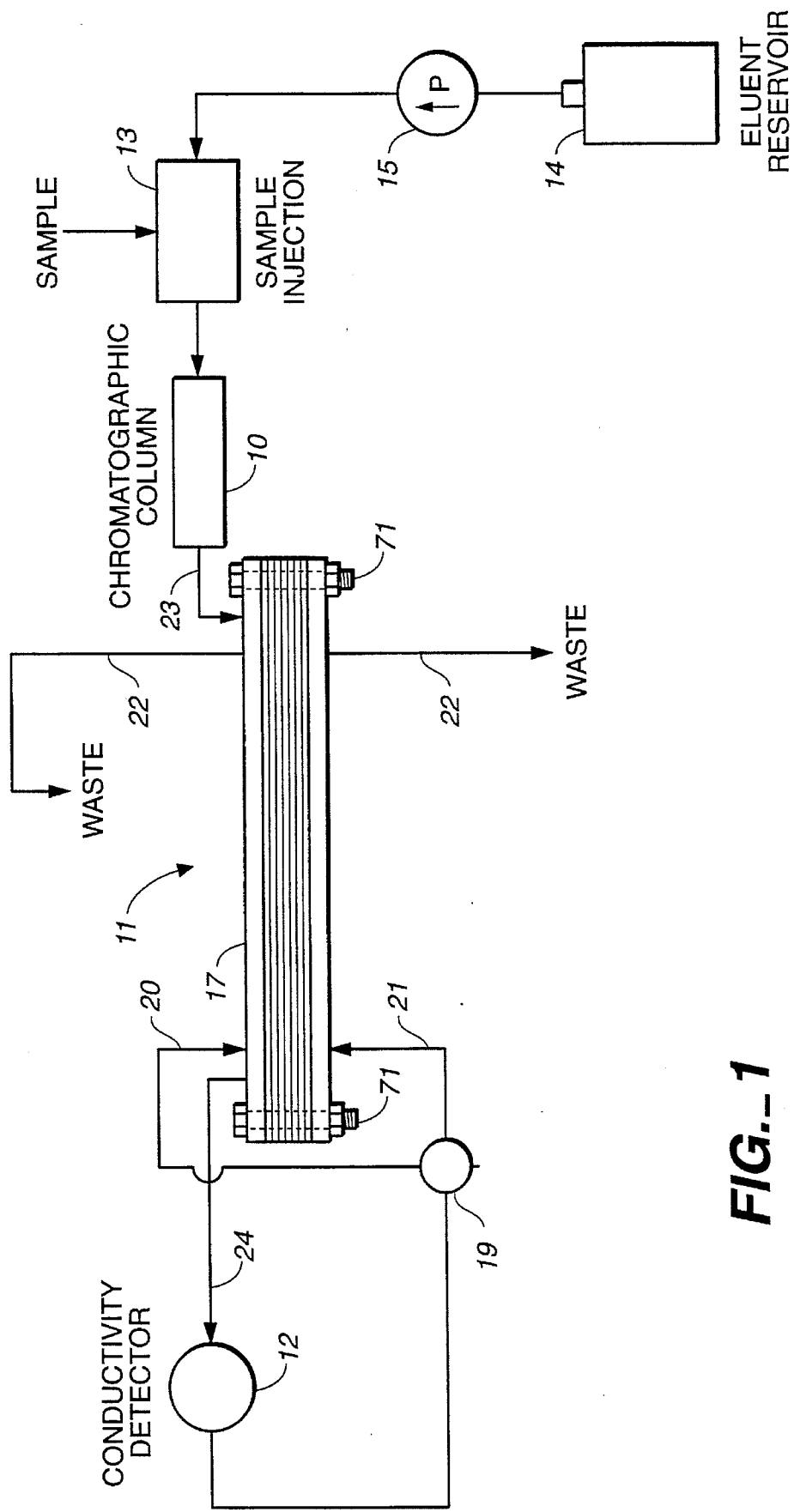
FIG._1

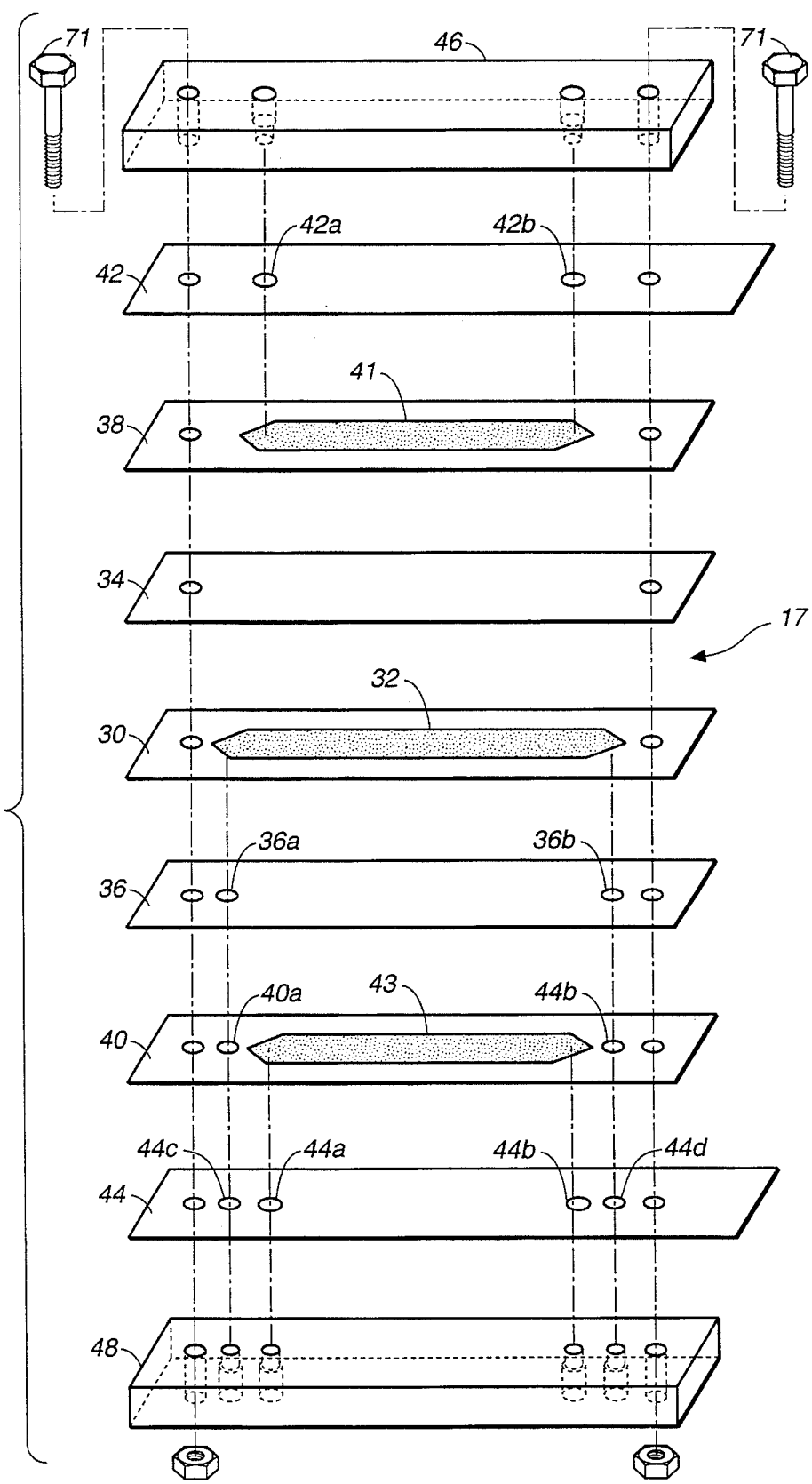
FIG._2

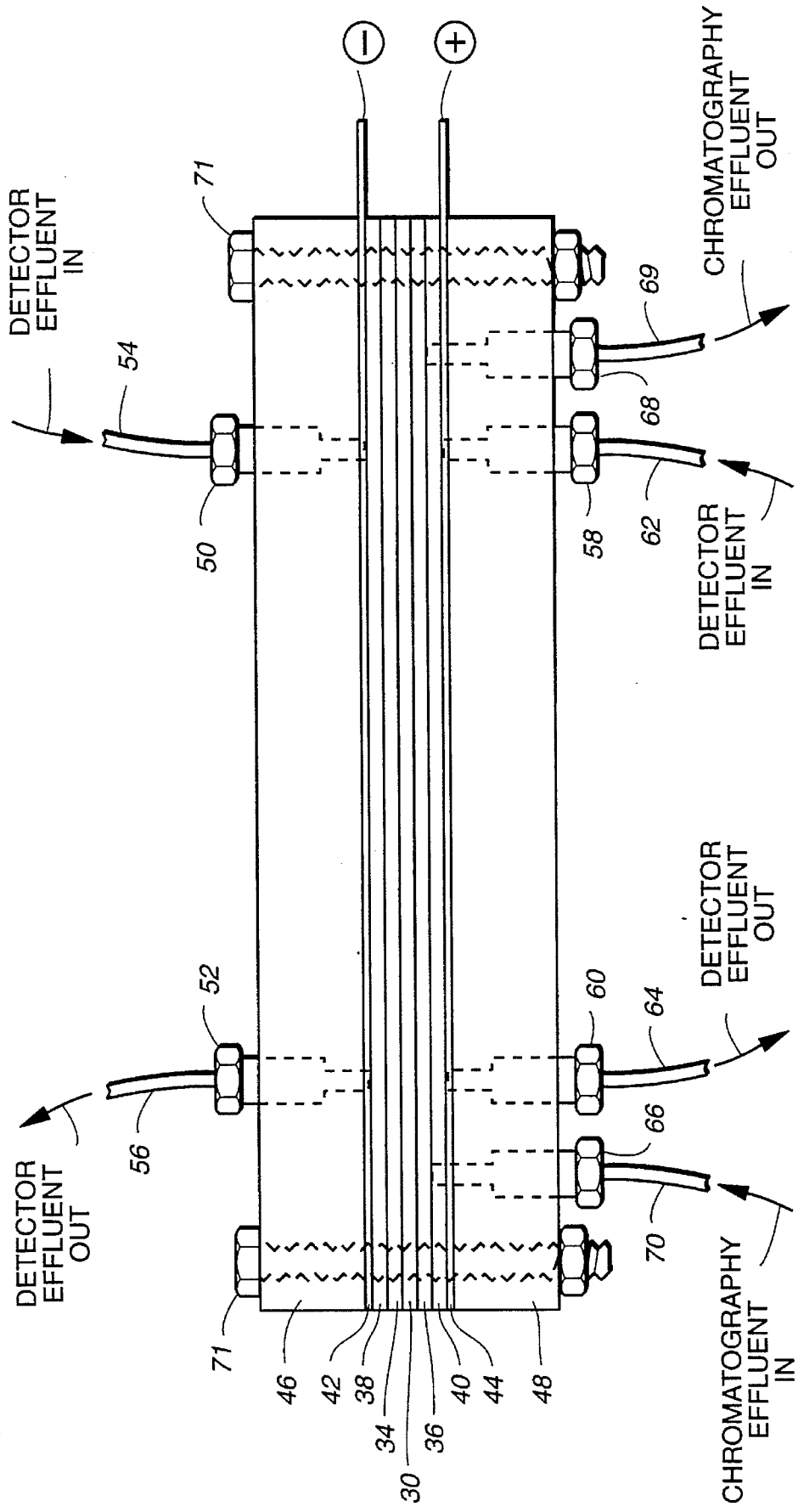
FIG._3

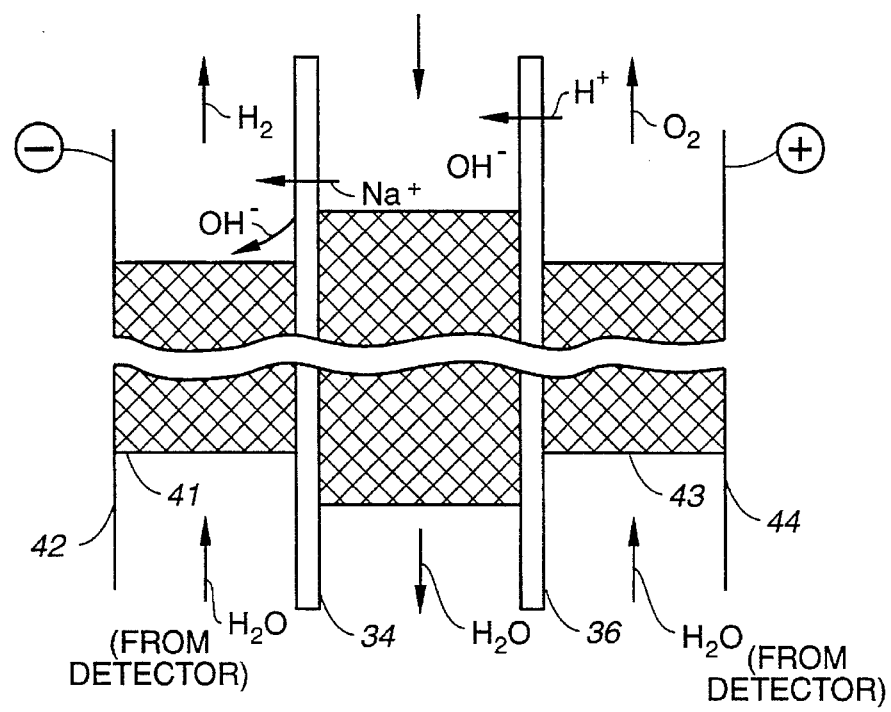
FIG._4
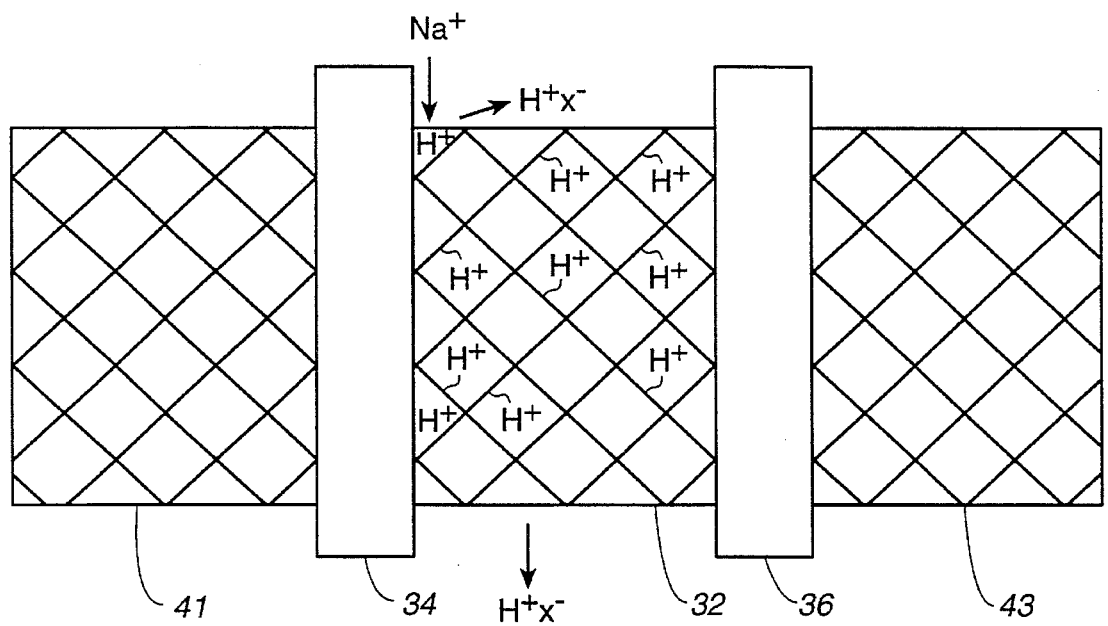
FIG._5

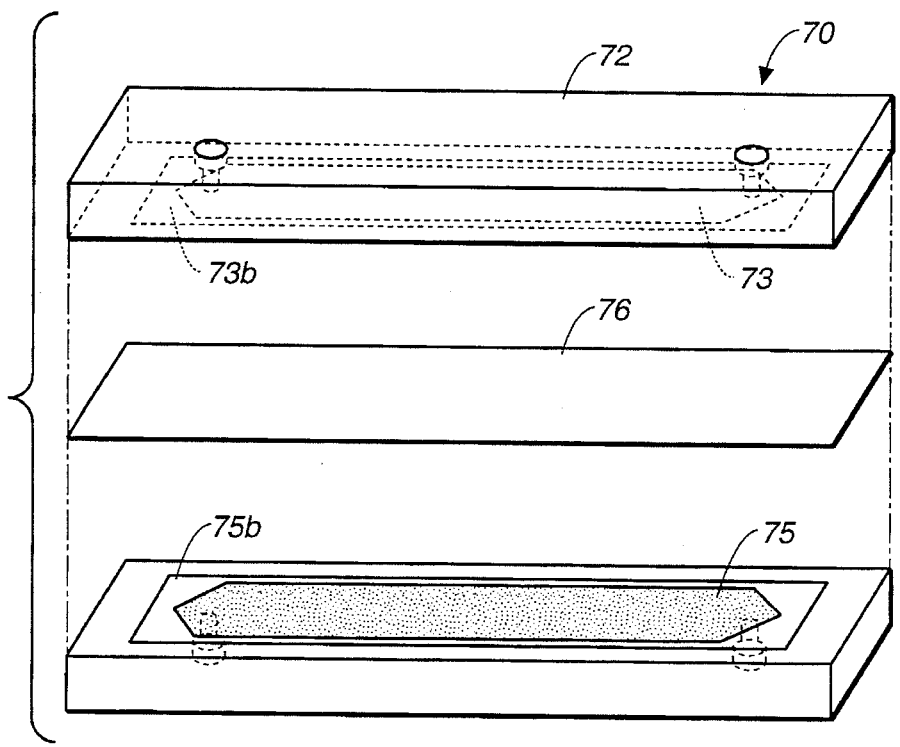
FIG._6
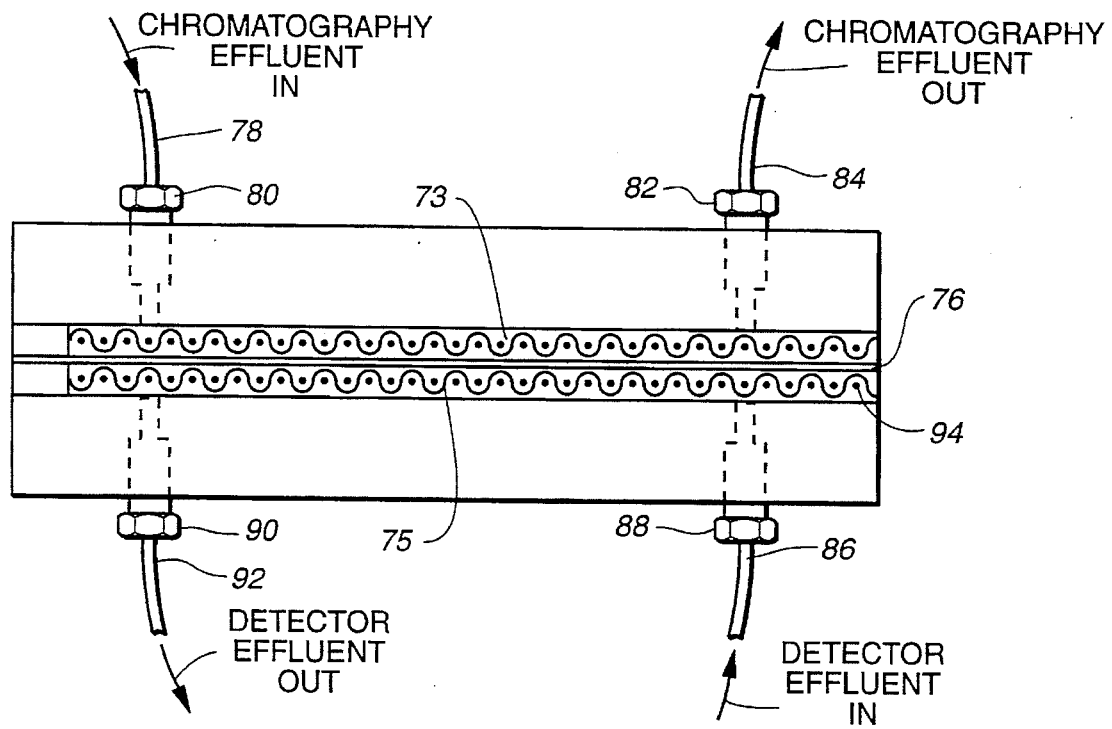
FIG._7

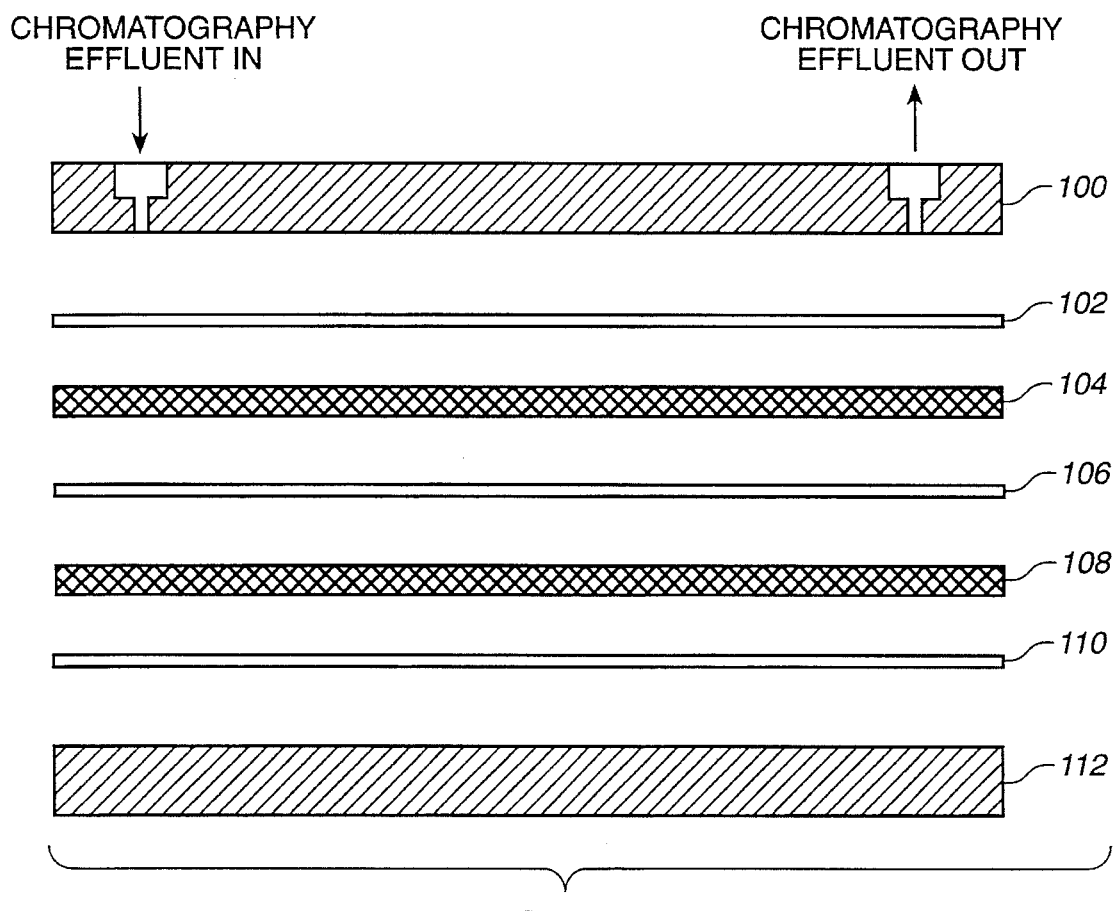
FIG._8
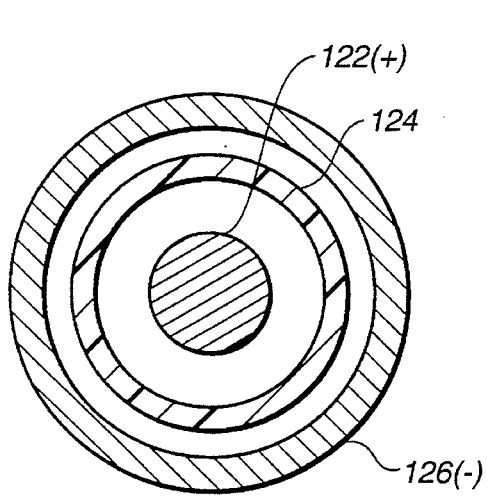
FIG._9
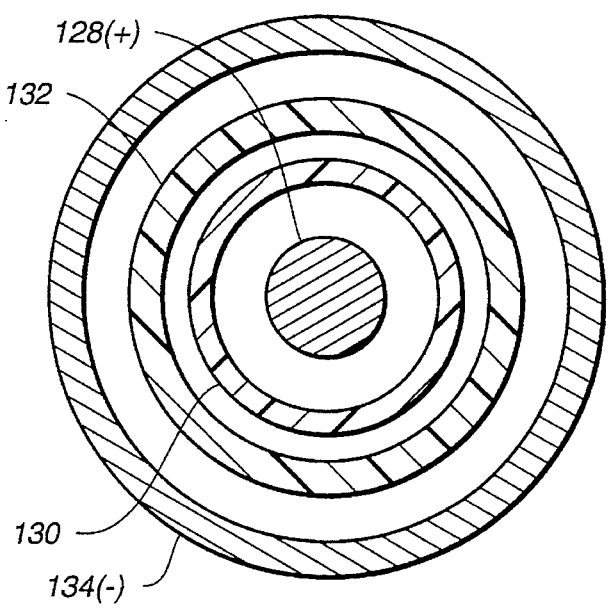
FIG._10

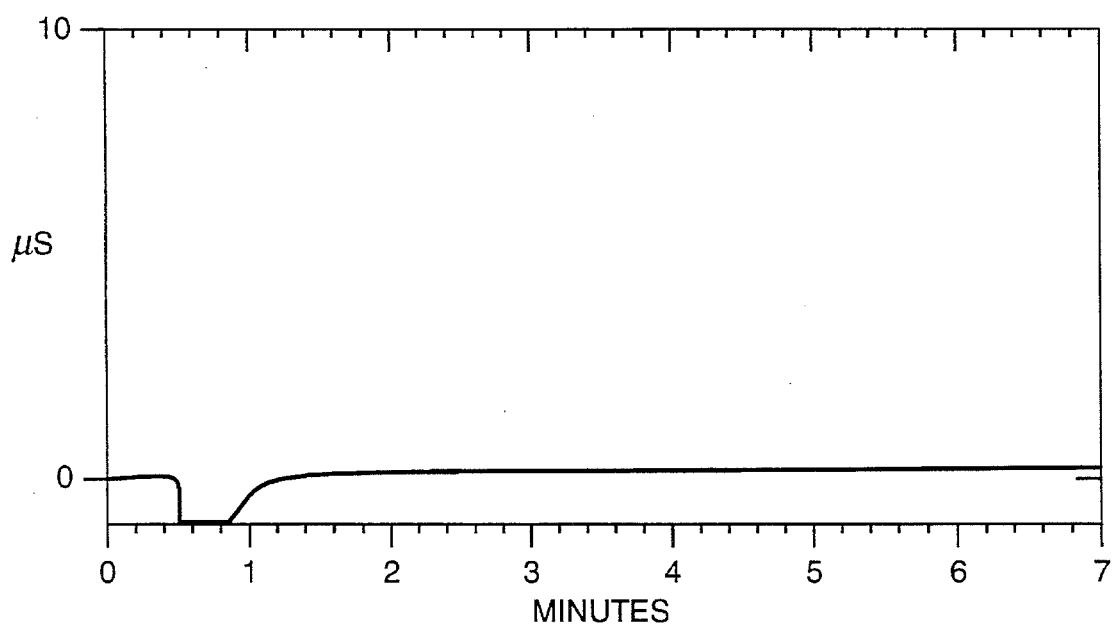
FIG._11a
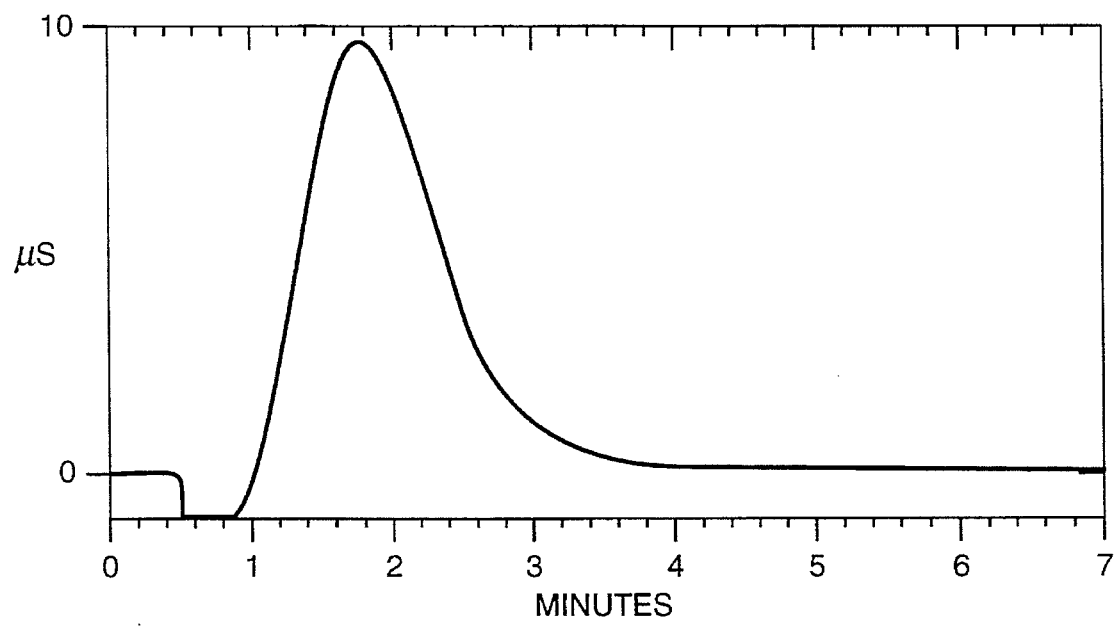
FIG._11b

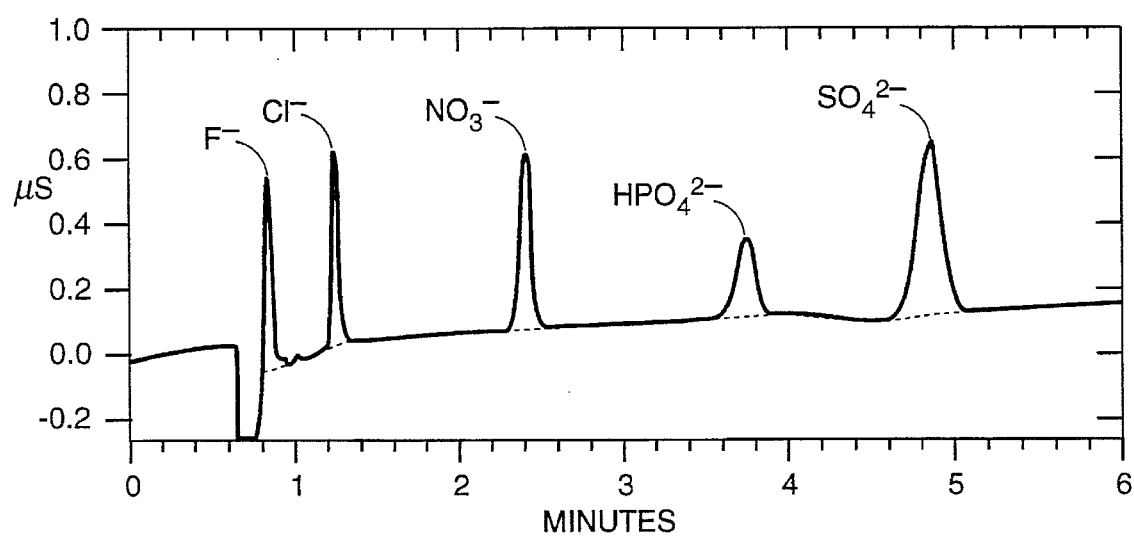
FIG._12
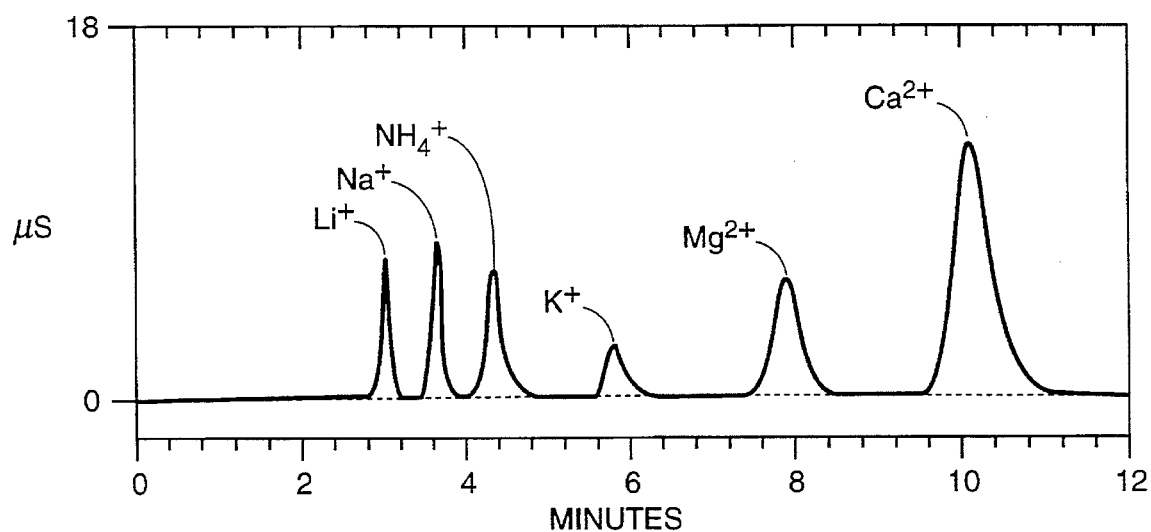
FIG._13

INTERMITTENT ELECTROLYTIC MEMBRANE SUPPRESSOR REGENERATION FOR ION CHROMATOGRAPHY

BACKGROUND OF THE INVENTION

The present invention relates to method and apparatus using suppression of eluents for the analysis of anions or cations in ion chromatography.

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed but not that of the separated ions so that the latter may be determined by a conductivity cell. This technique is described in detail in U.S. Pat. Nos. 3,897,213, 3,920,397, 3,925,019 and 3,926,559.

Suppression or stripping of the electrolyte is described in the above prior art references by an ion exchange resin bed. The bed requires periodic regeneration by flushing with an acid or base solution.

A different form of suppressor column is described and published in U.S. Pat No. 4,474,664, in which a charged ion exchange membrane in the form of a fiber or sheet is used in place of the resin bed. The sample and eluent are passed on one side of the membrane with a flowing regenerant on the other side, the membrane partitioning the regenerant from the effluent of chromatographic separation. The membrane passes ions of the same charge as the exchangeable ions of the membrane to convert the electrolyte of the eluent to weakly ionized form, followed by detection of the ions.

Another suppression system is disclosed in U.S. Pat. No. 4,459,357. There, the effluent from a chromatographic column is passed through an open flow channel defined by flat membranes on both sides of the channel. On the opposite sides of both membranes are open channels through which regenerant solution is passed. As with the fiber suppressor, the flat membranes pass ions of the same charge as the exchangeable ions of the membrane. An electric field is passed between electrodes on opposite sides of the effluent channel to increase the mobility of the ion exchange. One problem with this electrodialytic membrane suppressor system is that very high voltages (50–500 volts DC) are required. As the liquid stream becomes deionized, electrical resistance increases, resulting in substantial heat production. Such heat is detrimental to effective detection because it greatly increases noise and decreases sensitivity.

In U.S. Pat. No. 4,403,039, another form of electrodialytic suppressor is disclosed in which the ion exchange membranes are in the form of concentric tubes. One of the electrodes is at the center of the innermost tube. One problem with this form of suppressor is limited exchange capacity. Although the electrical field enhances ion mobility, the device is still dependent on diffusion of ions in the bulk solution to the membrane.

Another form of suppressor is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site to site transfer paths across the effluent flow channel so that suppression capacity is no longer limited by diffusion of ions in the bulk solution to the membrane. A sandwich suppressor is also disclosed including a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant. The patent also discloses the possibility of using water to replace the regenerant solution in the electrodialytic mode.

Another improvement in suppression is described in U.S. Pat. No. 5,248,426. This form of suppressor was introduced in 1992 by Dionex Corporation under the name "Self Regenerating Suppressor" (SRS). A constant current power controller generates an electric field across two platinum electrodes to electrolyze water in the regenerant channels. Functionalized ion-exchange screens are present in the regenerant chambers to facilitate electric current passage with permselective ion-exchange membrane defining the chromatography eluent chamber, as in the '098 patent. After detection, the chromatography effluent is recycled through the suppressor to form a flowing sump for electrolyte ion as well as providing the water for the electrolysis generating acid or base for suppression.

The history of ion chromatography suppression is summarized in Rabin, S. et al. J. Chromatog. 640 (1993) 97–109, incorporated herein by reference. One problem with electrochemical suppression is that it creates noise when power is applied during detection, for example in an SRS. Another problem is incompatibility of the electrolyte reaction with the presence of solvent in the eluent due to conductivity of oxidation products of the solvents.

SUMMARY OF THE INVENTION

The present invention relates to ion chromatography using electrochemical regeneration of the suppressor. A method is provided for reducing the background noise during detection caused by the application of an electric field using an electrolytic membrane suppressor. Ionic species in a water-containing eluent solution including electrolyte with transmembrane ions of opposite charge to the sample ionic species are separated on a chromatography column. The chromatography effluent is passed through the chromatography effluent flow channel of a suppressor in which such channel is separated by an ion exchange membrane containing exchangeable ions of the same charge as the transmembrane electrolyte ions, from at least one regenerant flow channel. Regenerant solution is directed through the regenerant flow channel. The effluent from the membrane suppressor flows through a detector in which the ionic species are detected. An electrical potential is applied between the chromatography effluent flow channel and the regenerant flow channel to assist diffusion of the transmembrane electrolyte ions through the ionic exchange membrane. Such electrical potential is applied prior to separation and detection for a sufficient time to convert the ion exchange material in the chromatography effluent flow channel to the hydronium or hydroxide form, $H^+$ or $OH^-$ being provided electrolytically from electrolysis of water in the electrolyte in the chromatography effluent flow channel. However, the electric field is discontinued during separation, suppression and detection of the injected sample. The system finds particular benefit in reducing background noise created during electrochemical suppression in an SRS. It is also useful for reducing the baseline interference when analyzing organic solvent-containing samples.

BRIEF DESCRIPTION OF THE DRAWINGS

FIG. 1 is a schematic view of apparatus for performing chromatography utilizing recycled detector effluent for the suppressor.

FIG. 2 is an exploded view of a sandwich suppressor device useful in the present invention.

FIG. 3 is a side view of a membrane suppressor illustrating chromatography effluent and detector effluent flow channels in dotted lines.

FIGS. 4 and 5 are schematic expanded views of the membranes and screens, respectively, showing simplified ion transfer in the electrochemical suppressor with power on prior to separation and detection and power off during detection, respectively.

FIGS. 6 and 7 are an exploded view and an assembled cross-section view, respectively, of a dual channel, single membrane suppressor device illustrating a channel.

FIG. 8 is a cross-sectional schematic view of another form of dual channel, single membrane device for use in the present invention.

FIGS. 9 and 10 are schematic cross-sectional views of two different tubular forms of electrodialytic suppressor.

FIGS. 11a, 11b, 12 and 13 are chromatograms illustrating the present invention.

DETAILED DESCRIPTION OF THE PREFERRED EMBODIMENTS

The system of the present invention is useful for determining a large number of ionic species so long as the species to be determined are solely anions or solely cations. A suitable sample includes surface waters, and other liquids such as industrial chemical wastes, body fluids, beverages such as fruits and wines and drinking water. When the term "ionic species" is used herein, it includes species in ionic form and components of molecules which are ionizable under the conditions of the present system.

The purpose of the suppressor stage is to reduce the conductivity, and hence noise, of the analysis stream background while enhancing the conductivity of the analytes (i.e., increasing the signal/noise ratio), while maintaining chromatographic efficiency. Thus, the following parameters bear upon the performance of the suppressor: (1) capacity of suppression, measured as µEq/min of eluent for each device; and (2) background conductivity measured as µS/cm per device. It is also important that the geometry of the device is such that analyte band dispersion is minimized.

The present invention relates to the intermittent use of the electric field during electrochemical suppression to minimize noise during detection of the ionic species. Specifically, it has been found that the suppressor can be regenerated to a sufficient extent to convert the chromatography electrolyte to weakly dissociated form so that detection can be performed in the absence of the electric field. This leads to a reduction in the background noise and significantly simplifies the regeneration process, eliminating the need for an external source of chemical regenerant. As used herein, the term intermittent electrochemical suppression will refer to this type of system.

Intermittent electrochemical suppression is particularly effective in reducing the noise which can be created by the SRS system sold by Dionex Corporation. Accordingly, the present system will be described in terms of such a system as set forth in U.S. Pat. Nos. 5,248,426 and 5,352,360 (incorporated herein by reference). However, it should be understood that the present invention also is useful with a system using an independent source of regenerant solution without recycle.

Referring to FIG. 1, a simplified apparatus for performing the present invention is illustrated. The system includes chromatographic separation means, typically in the form of a chromatographic column 10 which is packed with a chromatographic separation medium. In one embodiment referred to above, such medium is in the form of ion-exchange resin. In another embodiment, the separation medium is a porous hydrophobic chromatographic resin with essentially no permanently attached ion-exchange sites. This other system is used for mobile phase ion chromatography (MPIC) as described in U.S. Pat. No. 4,265,634. An ion exchange site-forming compound, including hydrophobic portion and an ion-exchange site, is passed through the column and is reversibly adsorbed to the resin to create ion-exchange sites.

Arranged in series with column 10 is suppressor means 11 serving to suppress the conductivity of the electrolyte of the eluent from column 10 but not the conductivity of the separated ions. The conductivity of the separated ions is usually enhanced in the suppression process.

The effluent from suppressor means 11 is directed to a detector, preferably in the form of flow-through conductivity cell 12, for detecting all the resolved ionic species therefrom. A suitable sample is supplied through sample injection valve 13 which is passed through the apparatus in the solution of eluent from eluent source or reservoir 14 drawn by pump 15, and then passed through the sample injection valve 13. The chromatography effluent solution leaving column 10 is directed to suppressor means 11 wherein the electrolyte is converted to a weakly conducting form, suppressor means 11 and passes through conductivity cell 12.

In conductivity cell 12, the presence of ionic species produces an electrical signal proportional to the amount of ionic material. Such signal is typically directed from the cell 12 to a conductivity meter, not shown, thus permitting detection of the concentration of separated ionic species.

The effluent from conductivity cell 12, referred to herein as the detector effluent, is directed to at least one flow-through detector effluent channel in ion-exchange membrane device 17. The membrane device will be described in detail hereinafter. The detector effluent flows through a splitter valve or tee 19 which separates the detector effluent into two different conduits 20 and 21 to supply the detector effluent to the detector effluent flow-through passages of the suppressor and then to waste through conduit 22. Alternatively, the detector effluent flows through the detector effluent chambers sequentially then to waste. The chromatography effluent flows from chromatographic column 10 to membrane device 17 through conduit 23, and from the membrane device to the conductivity detector through conduit 24.

Referring to FIGS. 2–5, a device is illustrated in the form of a sandwich suppressor device including a central chromatography effluent flow channel defined on both sides by ion-exchange membranes to the exterior of which are two detector effluent flow channels.

Referring specifically to FIGS. 2 and 3, membrane device 17 is illustrated which includes a central chromatography effluent flow channel flanked by detector effluent flow channels. Membrane device 17 includes means defining a chromatography effluent flow channel in the form of a chromatography effluent compartment, partially bounded by chromatography effluent gasket 30 defining a central cavity. To minimize dead space in the cavity it is preferable to form both ends of the flow channels in a peak or V-shape. Flow-through ion-exchange means, preferably bridging means in the form of chromatography effluent screen 32, is disposed in the cavity. Membrane sheets 34 and 36 are mounted to extend along opposite sides of chromatography effluent screen 32 and, together with gasket 30, define the outer perimeter of the chromatography effluent flow channel. Openings 36a and 36b are provided for effluent inlet and outlet, respectively, to the effluent flow channel.

Detector effluent gaskets 38 and 40 are mounted to the facing surfaces of membrane sheets 34 and 36, respectively, and define detector effluent flow channels. Bridging means may be provided in the detector effluent flow channels in the form of screens 41 and 43, respectively. Openings 40a and 40b are provided for inlet and outlet detector effluent flow through gasket 40. To simplify connections with the external flow lines, it is preferable to form the chromatography effluent flow channel slightly longer than the flanking regenerant flow channels.

As illustrated, spaced electrode means in the form of flat plate, wire or "grid" electrodes 42 and 44 are placed on the exterior sides of gaskets 38 and 40, respectively, extending substantially across the length and width of the chambers in the gaskets. An electrical potential is applied across the electrode means. Electrode 42 includes openings 42a and 42b to permit the inlet and outlet flow of detector effluent solution to the detector effluent flow channel in gasket 38. Similarly, electrode 44 includes inlet and outlet openings 44a and 44b, respectively, for detector effluent liquid flow and to the detector effluent flow channel and gasket 40, and also defines inlet and outlet openings 44c and 44d, respectively, for the chromatography effluent flow channel defined by gasket 30.

External support blocks 46 and 48 are formed of a rigid nonconductive material, such as polymethylmethacrylate, or polyether-ether ketone (PEEK) and serve to provide structural support for the remainder of membrane device 17.

Referring to FIG. 3, fittings 50 and 52 are provided for detector effluent inlet and outlet lines 54 and 56, respectively. Similarly, fittings 58 and 60 are provided for detector effluent inlet and outlet lines 62 and 64, respectively. Fittings 66 and 68 are provided for chromatography effluent inlet and Outlet lines 70 and 69, respectively. The fittings may be mounted to the support blocks by any conventional means such as mating screw threads.

The above assembled sheets and gaskets are mounted under pressure supplied by bolts 71 to form liquid-tight seals. Also, by use of such pressure in combination with appropriate sizing of the screen (or other bridging means described below) in comparison to the flow channel dimensions, the screen extends substantially the entire distance across the flow channels and contacts the membranes, resulting in significantly improved ion transport and efficiency. It is preferable for maximum membrane transfer efficiency to connect the lines to the chromatography effluent and detector effluent flow channels for counter-current flow.

Detector effluent gasket 30 may be formed of any suitable material which provides a liquid seal for the chromatography effluent flow channel which it defines. A suitable material for the gasket is a flexible liquid silicone-based rubber such as supplied under the name RTV by General Electric Co. or a plastic sheet such as "Parafilm" supplied by American Can Co. A similar material may be used for detector effluent gaskets 38 and 40.

Ion-exchange membrane sheets 34 and 36 may be of a type such as disclosed in U.S. Pat. Nos. 4,486,312 and 4,999,098. In particular, such sheets may be cation-exchange or anion-exchange membranes with polyethylene-, polypropylene-, or polyethylene-vinylacetate-based substrates. Other suitable substrates include polyvinylchloride- or polyfluorocarbon-based materials. The substrate polymer is solvent and acid- or base-resistant. Such substrates are first grafted with suitable monomer for later functionalizing. Applicable monomers include styrene and alkylstyrenes such as 4-methylstyrene, vinylbenzylchloride or vinylsulfonates, vinylpyridine and alyklvinylpyridines. As an example, to form a cation-exchange membrane, the sheets grafted with styrene monomers are functionalized suitably with chlorosulfonic acid, sulfuric acid, or other $SO_2$ or $SO_3$ sources. To form an anion-exchange membrane, the sheets grafted with vinylbenzylchloride monomers are functionalized with alkyl tertiary amines Such as trimethylamine or tertiary alkanolamines, such as dimethylethanolamine. Particularly effective membranes are no more than 10 mils thick, and preferably no more than 2–4 mils when wet.

Chromatography effluent screen 32 may be formed integral with chromatography effluent gasket 30 or may be inserted independently into the effluent flow channel. A screen integral with the surrounding gasket material may be formed by cutting a gasket from plastic sheet to include the desired flow path and pressing this gasket into a rectangular piece of screen such that only the flow path is not covered by the gasketing material.

Detector effluent screens 41 and 43 may be formed in the same manner as set forth with respect to chromatography effluent screen 32.

The flow-through ion-exchange means, preferably in the form of bridging means, includes continuous portions which extend substantially the entire distance across the chromatography effluent flow channel transverse to flow. In the embodiment of FIGS. 2 and 3, this distance extends between membrane sheets 34 and 36. In the alternate embodiment of FIG. 6 described below, only one membrane separates one regenerant flow channel from the effluent flow channel. There, the transverse distance spanned by the bridging means is from the membrane to the opposite wall defining the chromatography effluent flow channel. The bridging means defines a continuous convoluted flow-through passageway in the chromatography effluent flow channel along substantially the entire length of the membrane. This creates turbulence and thus increases the efficiency of mixing and transfer of the ions across the membrane as described below. The physical configuration of the screen may vary so long as its bridging function and turbulence-producing function are accomplished. Thus, the screen may be provided with a weaving pattern either perpendicular or diagonal to the direction of flow. Also, the fibers may be smooth or contain protrusions such as bumps.

A major function of the flow-through ion-exchange means is to provide a site-to-site path for ions in the direction transverse to the chromatography effluent flow channel to increase the efficiency of ionic transfer across the ion-exchange membrane as more fully described below. Bridging means in the form of a screen may be functionalized for this purpose in a manner analogous to the functionalization of the ion-exchange membranes set forth above. Suitable screens may be formed of the same base polymers grafted with the same functionalizing monomers as those set out above for the membranes.

The maximum chromatographic efficiency of the screen embodiment of the flow-through ion-exchange means may be achieved using a relatively small mesh (measured after functionalization), e.g. on the order of 110 μ mesh size or less with relatively thin fibers, e.g., on the order of 0.004 inch in diameter. An open area in the flow channel on the order of 5% to 50% (preferably about 15%) provides excellent efficiencies. A suitable proportion of grafting monomer to grafting polymer substrate is on the order of 5%–50% (preferably about 25% to 35%). In order to obtain maximum efficiency, the effluent flow channel should be fairly narrow, e.g., on the order of about 0.5 to 1.0 cm, with the weave pattern oriented diagonally to the direction of flow. As the exposed membrane surface area increases, suppression capacity increases. However, practical limits are prescribed by known principles of chromatography. For example, to minimize band broadening, a minimum volume is desired.

To maximize the dynamic capacity, the regenerant screens may be functionalized to relatively high ion exchange capacity, e.g. 2 mEq/g. Also, as with chromatographic efficiency, it is preferable to orient the fibers of the screen diagonally to the direction of flow.

Parameters relevant to the screen's function are set out in U.S. Pat. No. 4,999,098, incorporated herein by reference.

In the embodiments of FIGS. 2 and 3, an electrical potential from a direct current source (not shown) is applied between electrodes 42 and 44 from any suitable source. The electrodes are formed of highly conductive material which is inert to the solutions being passed through the membrane suppressor. Platinum is a preferred electrode material for this purpose.

In one mode of operation, power is applied between chromatographic runs and power is turned off during a given chromatographic run. In the suppressor device 17, effluent from chromatographic column 10 is directed through the chromatography effluent flow channel bounded on both sides by ion-exchange membranes 34 and 36 partitioning the detector effluent from the chromatography effluent. The detector effluent flows from the conductivity cell through the detector effluent channels. The membrane is preferentially permeable to ions of the same charge as the exchangeable ions of the membrane and resists permeation of ions of opposite charge. The exchangeable ions of the screens and membranes are in the ion form necessary to convert the developing reagent of the eluent to a weakly ionized form. During a chromatographic run, the chromatography effluent from chromatographic column 10 is passed through the chromatography effluent flow channel and contacts both membranes, and the ion exchange screen in the chromatographic effluent flow channel, exchanging the ions in the developing reagent for ions on the screen and membranes, thus converting the developing reagent to a weakly ionized form. The resolved ionic species in the effluent leaving the suppressor device are detected, as with a conductivity detector. The membranes are simultaneously contacted on their outer sides with the detector effluent flowing in the opposite direction through the detector effluent flow channel so that the membrane forms a selective permeability partition between the detector effluent and the chromatography effluent. After a chromatographic run is complete, power is turned on and ions extracted from the chromatographic effluent during the run at the ion-exchange sites of the screens and membranes are diffused through the membranes and are replaced with ions electrolytically generated from the detector effluent. Application of a potential across the electrodes increases the mobility of the ions across the membrane, speeding the regeneration process.

FIG. 4 schematically illustrates the electrochemical operation of the present invention for a particular system, using a sandwich suppressor with screens in the chromatography effluent and detector effluent channels, and applying an electrical potential between spaced electrodes as a means to regenerate the suppressor before analysis. The system illustrated is for anion analysis and includes sodium hydroxide as the electrolyte of the effluent to be converted into weakly ionized form ($H_2O$) in the suppressor. Thereafter, the solution passes through the conductivity cell and is recycled to the detector effluent flow channel. The ion-exchange membrane sheets allow the positively charged sodium and hydronium ions to permeate across the membrane.

Hydroxide ions in the chromatographic effluent tend not to permeate the membrane sheet because of Donnan Exclusion forces. Hydronium ions generated in the anodic detector effluent compartment are drawn to the cathode and pass through the cation exchange membrane into the chromatography effluent flow channel where they combine with hydroxide ions to form water. Thus, the sodium hydroxide stream is converted to deionized water in the chromatography effluent flow channel. The sodium ions permeate the cation exchange membrane sheet and are dispersed in the negatively-charged cationic detector effluent flow channel as NaOH and thus ultimately routed to waste through the detector effluent outlet lines. Applying a potential across electrodes 42 and 44 generates the required hydronium and hydroxide ions and increases the kinetics of ion flow across the membrane and thereby increases capacity and, thus, the suppression efficiency of the suppressor device.

No analyte anions are illustrated in FIG. 4 because the power is only activated when not performing a chromatographic run.

In operation of the system of FIG. 4, in the positively charged detector effluent flow channel, hydronium ion is generated for passage through membrane 36 according to the following equation:

$$6H_2O \rightarrow 4H_3O^+ + O_2 + 4e^- \quad (1)$$

In the chromatography effluent flow channel, the sodium ion passes through membrane 34 under the influence of the cathode. Hydroxide is converted to water according to the following equation:

$$OH^- + H_3O^+ \rightarrow 2H_2O \quad (2)$$

In the negatively-charged detector effluent flow channel, the sodium ion from the chromatography effluent flow channel is converted to NaOH with hydroxide ion produced by the following equation:

$$4e^- + 4H_2O \rightarrow 4OH^- + 2H_2 \quad (3)$$

Screens 32, 41 and 43 provide the capacity for the suppressor device to remove ions from the chromatography effluent stream during suppression while the power is turned off. The threads of the screen preferably extend substantially across the chromatography effluent flow channel transverse to flow to contact both membranes. In the illustrated device, the chromatography effluent screen extends the distance between membranes 34 and 36. The functionalized screens include exchangeable ions of the same charge as those of the membranes. In this manner, the screen provides a direct site-to-site contact between the membrane walls for the ions to be diffused through the membranes while power is on during regeneration. The capacity of the system is significantly increased by the use of such functionalized screen in the detector effluent flow channel. The capacity is increased by using the same types of screens in the regenerant flow channel.

A system of the above type using continuous current application and recycling the effluent from the detector to the suppressor is set forth in U.S. Pat. Nos. 5,248,426 and 5,352,360. The present system is also applicable to the use of an external water source for the detector effluent flow channel.

The potential to be applied to the electrodes in the above system may be relatively low due to the presence of the functionalized bridging means in the effluent channel. However, since the electrical power is off during detection, more power is required than for the prior art systems in which the power is on continuously to substantially regenerate the screens and membranes. Typical conditions for regeneration include a voltage of about 3–50 VDC (preferably about 5–15 VDC), and a current of 20–1000 mA (preferably 100 to 500 mA). The electrical potential is applied for a sufficient time and at a sufficient voltage to provide sufficient regeneration of the ion exchange sites in the screen in the chromatography effluent flow channel to the hydronium ion form, so as to accomplish suppression during a chromatographic run while the power is discontinued. Thus, it is necessary during power actuation to permit conversion of the electrolyte in the chromatography effluent flow channel to weakly dissociated form during the subsequent suppression and detection stage in which power is off. The underlying theory that permits the power to the suppressor to be off while collecting data is that excess capacity of hydronium ions is provided to ion exchange sites in the suppressor during the time while the power is on. Thus, when the power is at a relatively high power setting (e.g., 500 mA) complete regeneration may be accomplished in about 2 to 5 minutes, including equilibration time. This permits lower noise, thus greater sensitivity, For example, intermittently powered SRS (including recycle) may be adjusted to have comparable sensitivity to the SRS system using an external water source as a regenerant solution.

The basic principle underlying the invention is that the SRS contains a large reserve of hydronium ions (for anion analysis) or hydroxide ions (for cation analysis) that are available for suppression on the ion exchange sites. The driving forces for suppression in this mode are the neutralization and ion exchange reactions illustrated in FIG. 5. This is the typical operation of the anion SRS, with hydronium and hydroxide ions generated at their respective electrodes. Hydroxide ions from the eluent are neutralized by the generated hydronium ions, and the sodium counter-ions are attracted to the negative electrode and leave with the generated hydroxide ions.

When power is discontinued, there is a sufficient reserve of hydronium ions (for anion analysis) or hydroxide ions (for cation analysis) in the screens and membranes to provide suppression. The electrolyte in the chromatography effluent is neutralized by the suppression ions on the screens and membranes, forming a weakly dissociated species, and the counter-ions to the electrolyte replaces the ions used to perform the suppression, thus removing them from the effluent. When a sample passes through the chromatography effluent flow channel, the counter-ions to the sample ions of interest exchange with suppression ions on the screens and membranes. The pairing of suppression ions with strong acid (anion analysis) or strong base (cation analysis) sample ions serves to increase the overall conductometric signal due to these ions.

When power is resumed, the counter-ions from the chromatography effluent electrolyte and samples are replaced on the ion exchange sites on the screens and membranes by hydronium ions (for anion analysis) or hydroxide ions (for cation analysis) electrolytically generated. Sufficient time is allowed with power on to replenish the reserve of ions.

FIG. 5 illustrates the SRS system with the power discontinued. During the time that the analyte ionic species are being separated, suppressed and detected, no additional ions are being generated. However, there is excess capacity in that a large proportion of the ion exchange sites on the membranes and flow-through ion exchange means (e.g., ion exchange screens) are in the hydronium ion form. Typically, immediately after the power is turned off, the percentage of such sites in the hydronium form are from about 75 to 95 and preferably from about 90 to 95. It is important that there be sufficient capacity of hydronium ions in such ion exchange sites to permit conversion of the electrolyte in the chromatography in the effluent flow channel to weakly dissociated form during suppression when the power is off. Thus, after discontinuing the power, flowing the solution containing sodium hydroxide through the chromatography effluent channel causes the hydronium ions to neutralize the hydroxide ions and be replaced on the ion exchange sites by the sodium counter-ion. This can continue until the hydronium ions are exhausted, at which time the base line rapidly increases and the SRS ceases to suppress.

When the power is on with the sodium hydroxide eluent flowing through the system, an equilibrium is reached where a small portion of the membranes and screens in the chromatography effluent channel (e.g., about 5 to 15% on the upstream side) are in the sodium ion form while the remainder is in the hydronium form. This profile is constant when equilibrium is achieved with the power on. When the power is off, the upstream portions of the membranes in the sodium form increase relative to the remainder of the membranes and screens as the sodium ion slowly replaces the hydronium ion and a sodium ion front moves through the suppressor as electrolyte is suppressed. Since there is a sufficient reserve of hydronium ions for suppression, the device continues to suppress until essentially all of the hydronium ions on the screens and membranes are replaced by sodium ions.

In treating sequential samples, the power to the suppressor is periodically turned on at any suitable time during the cycle other than detection of the analyte ions. Thus, an appropriate balance is reached between the time and power requirements necessary to provide the capacity to suppress during detection when the power is off. The higher the power, the shorter the time necessary for this purpose. An effective suitable cycle is for the power to be turned on at all times except when the detector is on.

A typical event profile, using a low concentration carbonate/bicarbonate eluent, is set forth in Table 1 in Example 1.

While the above sandwich suppressor embodiment includes a central chromatography effluent flow channel separated by two membranes from two coextensive detector effluent flow channels, the system is also applicable to the use of a single detector effluent flow channel separated from the chromatography effluent flow channel by a single membrane.

Referring to FIGS. 6 and 7, another embodiment of suppressor means 70 is illustrated using a flow channel with integral projections protruding from the wall. Suppressor means 70 includes upper rigid support block 72 with chromatography effluent flow channel with integral projections and wall 73 and lower support block 74 with detector effluent flow channel wall 75, separated by an ion-exchange membrane 76 of the type described above.

The chromatography effluent flows into the suppressor device through effluent inlet 78, fitting 80 and flows along chromatography effluent flow channel defined by wall 73, through channel 94 containing projections and then through fittings 82 and out chromatography effluent outlet line 84. Similarly, detector effluent solution flows from inlet line 86 through fittings 88 across the detector effluent flow channel defined by wall 75, out fitting 90 and through detector effluent outlet 92 to waste. Means, not shown, are provided for applying an electrical potential between the detector effluent flow channel and the chromatography effluent flow channel. The device of FIGS. 6 and 7 is used in the overall system of FIG. 1 in place of the device of FIGS. 2–5, with the principal functional difference being the use of only a single detector effluent flow channel.

The liquid flows through the channels formed by the spacing among the projections. The dimensions of the projections and spacing are selected to provide the desired frequency of contacts with the flowing ions to increase their mobility across the membrane and to create sufficient turbulence for increased mixing efficiency. The advantage of this design is simplicity of assembly.

Another dual channel membrane suppressor device may be used in place of the sandwich suppressor of FIGS. 2–5. The mode of construction is the same as the device illustrated in FIGS. 2–5 with the exception that one of the detector effluent flow channels is eliminated. Thus, this can be accomplished by removing membrane 36 and screen 43 of FIG. 2. One of the reasons that a single detector effluent flow channel can be used is the intermittent application of the electrical potential. Thus, gasses produced during electrolysis for regeneration can be flushed out before injection of the next sample for analysis.

A suppressor of the above general type is illustrated in FIG. 8. As described for anion analysis, from top to bottom the suppressor includes a top external support block 100, negative electrode 102, cation exchange screen 104, cation exchange membrane 106, cation exchange screen 108, positive electrode 110, and bottom external support block 112. Eluent flows through the lower chamber 114 defined between block 112 and membrane 106 for neutralization using hydronium ions on screen 108 for suppression. Water (suppressed eluent) from the detector is a suitable source from the flowing aqueous stream in chamber 114, providing water for electrolysis at the negative electrode. After completion of the analytical run, the power can be applied. Positive electrode 110 regenerates screen 108 with hydronium ions. At the same time, sodium ions from the eluent that have been retained by the ion exchange sites are displaced in flow-through membrane 106 and flow out of the suppressor after association with hydroxide ions generated at negative electrode 102. The unit of FIG. 8 could operate in a single device "recycle" mode. The only waste product would be oxygen and water with substantially no ions being sent to waste from chamber 114. This water could be used as the source of water for electrolytic production of hydroxide ions used to remove the sodium ions from the suppressor. In that regard, it would have similar utility to an SRS device operating in the intermittent mode.

Suitable eluent solutions for anion ion chromatography include alkali hydroxides, such as sodium hydroxide; alkali carbonates and bicarbonates, such as sodium carbonate; alkali borates, such as sodium borate; combinations of the above; and the eluent systems of the aforementioned patents.

The recycle system of the present invention is also applicable to the analysis of cations (e.g., lithium, sodium, ammonium, potassium, magnesium, and calcium). In this instance, the electrolyte of the eluent is typically an acid which does not damage the membrane. Methane sulfonic acid has been found to be inert to the membrane under electrolytic conditions. Other acids such as nitric acid and hydrochloric acid produce electrochemical by-products that may damage the membrane and are, thus, not generally preferred for that typical membrane.

In cation analysis, the flow of the electrolyte ion is from the cathode toward the anode, rather than the reverse as in anion analysis and the ion exchange screens and membranes are aminated and permeable to anions. Thus, in the negatively-charged detector effluent flow channel, water is converted to hydroxide ion and hydrogen gas. The hydroxide ion passes through the adjacent membrane into the chromatography effluent flow channel and combines with hydrogen ion (or an amine or other basic organic molecule group) to form weakly ionized electrolyte. The negatively-charged transmembrane ion travels through the second membrane into the positively-charged detector effluent flow channel under influence of the anode to form an acid which passes to waste. In summary, for cation analysis, the electrical charges of the analyte, eluent reagent, and membranes are reversed, as compared to anion analysis.

A dual channel membrane suppressor is useful because the assembly has fewer parts and is easier to assemble. However, gases are generated in the chromatography effluent which can interfere with detection in the conductivity cell. For example, for ion analysis, oxygen is generated in the detector effluent flow channel. One way to remove the oxygen is to pass the effluent from the chromatography effluent flow channel through a gas diffusion removal device, using a gas diffusion membrane, prior to reaching the conductivity cell. One such device is disclosed in the U.S. Pat. No. 5,045,204. In another embodiment, a gas diffusion membrane forms a wall defining the opposite side of the chromatography effluent flow channel from the ion exchange membrane. An inert gas stream, such as nitrogen, may be flowed in a channel bounded on one side by the gas diffusion membrane, preferably countercurrent to the chromatography effluent flow. In this manner, the solution leaving the chromatography effluent flow channel is degassed prior to reaching the conductivity cell. In either event, a suitable gas diffusion membrane is sold under the trademark Accural® or Celgard®. The problem with gas diffusion removal devices is that they add significant extra volume to the chromatography flowstream, compromising analyte peak efficiency.

The use of intermittent current can eliminate the need for such gas diffusion membranes. Specifically, the system can be equilibrated by flowing eluent after regeneration and before injection of the new sample. Equilibration removes the gas which can interfere with detection.

The above system for anion orcation analysis illustrates an ion exchange screen as the preferred flow-through ion exchange means. However, it should be understood that other ion exchange means may also be employed for the sandwich suppressor or other relatively flat or tubular form membrane-based suppressor. For example, ion exchange particles may be packed in the flow channels for this purpose. Here, it would be preferable to include some mode to keep the ion exchange particles in the device by using a porous polymeric support that has smaller pores than the resin being used, such as sintered polyethylene available from General Polymeric.

Referring to FIG. 9, a schematic cross-sectional view of a tubular form of the electrodialytic suppressor of the present invention is illustrated. In this instance, it is assumed that the chromatography effluent channel is the lumen of the innermost tube. The device includes anode 122 (in the form of a rod or wire, e.g., formed of platinum, gold, carbon or stainless steel), cation exchange membrane 124, and outer wall 126 which may be formed of a conductive material to serve as the cathode. Preferably, flow-through ion exchange means in the form of ion exchange resin is disposed in the chromatographic effluent flow channel, the detector effluent flow channel or both. This system is comparable in general function to the one illustrated in FIG. 4. Alternatively, the detector effluent flow channel may be the lumen of the inner tube. In this instance, the polarities of the electrodes are reversed. Membrane 124 may be formed of stretched or unstretched tubular ion exchange membranes, e.g., Nation 811X from Perma-Pure Products, N.J. Outer wall 126 may be formed of an 18 GA. stainless steel (SS) tubular case.

FIG. 10 illustrates a tubular type of dual-membrane suppressor of similar function to the sandwich membrane suppressor. It is generally constructed by inserting a length of suitably inert wire inner electrode 128 into a length of tubular inner membrane 130 which is itself inserted inside a length of somewhat larger diameter tubular outer membrane 132 and enclosing the whole assembly in the stainless steel tube 134 of appropriate dimensions. The outer tube itself functions as the electrode, connections being made at the ends to allow access to the flow channels between the inner electrode and inner membrane, between the two membranes (annulus) and between the outer membrane and stainless steel case.

A major advantage of the foregoing invention is that it reduces background noise during detection for a recycling SRS system. For maximum benefit, it is preferable that the sole source of solution in the detector effluent flow channel be the effluent from the detector. In that embodiment, there is a one-to-one equivalent of flow through the detector effluent flow channel and through the chromatography flow channel. If desired, in some systems this flow rate could be increased by supplementing the solution flow through the effluent flow channel. Alternatively, the system could be operated with an external source of solution supplied to the detector effluent flow channel and without any recycle.

The power requirements for this system are dependent to some extent upon the flow rate through the system and the concentration of electrolyte solution. For this purpose, a suitable flow rate or chromatography effluent is about 0.01 to 10 mL/min. and, preferably, 0.25 to 2 mL/min. For such flow rates, suitable power requirements are 2.5 to 7 volts at 50 to 500 milliamps. This applies to both the flat membrane suppressor and tubular membrane assembly.

Other alternative configurations (not shown) of the suppressor can be used in accordance with the present invention. For example, referring to the suppressor of FIGS. 2–4, the positions of screens 41 and 43 may be reversed with the positions of electrodes 42 and 44, respectively. Specifically, in such alternative configurations, electrodes 42 and 44 extend along, and are pressed flush against, ion exchange membranes 34 and 36, respectively. The electrodes are in contact with the solution flowing through the outside detector effluent flow channels. In this instance, the electrodes include openings to permit ion transport across the ion exchange membranes between the outside detector effluent flow channels and the chromatograph effluent flow channels. Such openings may be formed in a number of known ways, e.g., by punching of spaced holes (typically from 0.010 inch to 0.250 inch across), or by forming the electrodes of a woven screen, or by notching an inert foil electrode so that the electrode forms a zigzag or serpentine pattern along the length of the chamber. For example, platinum wire bent into a zigzag pattern can be used, however, platinum or platinum plated foil is preferable to prevent excessive resistive heating.

In yet another embodiment (not shown), a suppressor may be formed in which one or both of the electrodes and screens in the outside flow channels are reversed from the configuration shown in FIGS. 2–4, such that the electrodes are against the membranes and the screens are against the external support block. The electrode and screen are in the configuration illustrated in Figures 2–4 for one of the outside flow channels while in the opposite outside flow channel the electrode and screen are reversed in the manner described in the previous paragraph. An effective hybrid configuration for an ion analysis is formed in which one or both electrodes with spaced openings in the form of a screen or grid is flush against the ion exchange membrane and the cathode (the compartment to the left of FIG. 3) is in the configuration illustrated in FIGS. 2–4. The same configuration is preferred for cation analysis.

EXAMPLE 1

In this example, a sandwich suppressor device as illustrated in FIGS. 2–5, suitable for anion analysis, is constructed for use in the system of FIG. 1. The cation-exchange screens 32, 41 and 43 are formed as follows. The base screen is of a polyethylene monofilament type supplied by Tetko, Inc. The screen mesh (the size of the screen opening) for the central screen 32 is 140 μm, and 410 μm for the outside screens 41 and 43. Such screen is immersed in a solution of 30% styrene w/w in methylene chloride solvent. Grafting occurs by irradiation with gamma rays at a dose of 10,000 rads/hour for about 48–120 hours at 80°–90° F. under nitrogen atmosphere. The screen is then soaked in 10% w/w chlorosulfonic acid in methylene chloride for 4 hours at about 40° C. The screen is then immersed in 1M KOH at 55° C. for 30 minutes.

The substrates for the ion exchange membranes 34 and 36 are film or sheet type made of PTFE (Teflon). The substrate polymer is solvent and acid or base resistant. Such film is first grafted with styrene monomer and then functionalized to form a cation-exchange membrane. Membrane functionalization and sulfonation are performed in the same manner as functionalizing the screens in the previous paragraph.

The gasket is formed of an inert, chemical resistant material suitable for providing a liquid seal for the flow channel it defines.

The overall hardware includes external support blocks made of a rigid nonconductive material (PEEK) serving to house the screens, membranes and electrodes. It also provides structural support for the suppressor. The top block has four fittings (one pair for the eluent inlet and eluent outlet and the other pair for regenerant inlet and regenerant outlet, respectively). The blocks are pressed together by conventional means, such as screws, to obtain a liquid-tight seal.

The subassemblies are formed as follows. A screen with surrounding gasket material is formed by cutting a gasket from plastic film that includes the desired flow path and pressing this gasket into the screen such that only the flow path is not covered by the gasket material. For each gasket two rectangles of ultra-low molecular weight polyethylene (Parafilm "M", American National Can Company) are cut with the appropriate dimensions of the flow channel also cut out. The screen is sandwiched between the Parafilm gaskets, and the stack is pressed to 20,000-30,000 psi at ambient temperature. One eluent screen/gasket assembly and two regenerant ones made with sulfonated screen and Parafilm are required per suppressor.

Two rectangles of cation-exchange membrane are cut to match the inlets and outlets of the flow path profile and the overall dimension of the screens. 3 mil thick polytetrafluorethylene (Teflon) base membrane is used.

An anode and a cathode made of 0.025 mm titanium foil plated with platinum, with measurements of 1.0 by 12.0 cm were used.

The system is in the form of a chromatographic column arranged in series with the suppressor. The solution leaving the column is directed to the suppressor wherein the electrolyte is converted to a weakly conducting form. The effluent is then directed to a detector in the form of a flow-through conductivity cell for detecting all the resolved ionic species. The effluent after passing through the conductivity cell is redirected to the inlet port of the outside channels in which the detector cell effluent is electrolyzed, supplying hydronium ions ($H^+$) for neutralization reaction. The electrical potential required to operate the suppressor was generated by a DC power supply unit (0–10 VDC).

The timing cycle is set forth in the following Table 1:

| Time (min) | Action |
| --- | --- |
| Init | SRS power on |
| 3.0 | SRS off, begin loading sample (Begin one minute equilibration) |
| 4.0 | SRS off, inject sample, begin collecting data (7 minute run time) |
| 11.0 | SRS power on, end data collection |

Programming of the intermittent power was performed by editing the "Timed Events" program in Dionex AI-450 software, written for the IBM-PC and Microsoft Windows.

A suppressor of the above type with central gasket 30 of dimension 1.0 cm wide ×14.3 cm long was run using an aqueous solution of 1.8 mM sodium carbonate/1.7 mM sodium carbonate as the eluent (simulating a chromatography effluent) at a flow rate of 2.0 mL/min. The left side of the following Table 2 illustrates peak to peak noise without power. The right side illustrates noise with power applied at 100 mA of current. The unpowered operation yields noise levels at least two times quieter.

| Power Run # | Off Pk-Pk Noise | Power Run # | On Pk-Pk Noise |
| --- | --- | --- | --- |
| 1 | 2.22 | 1 | 6.03 |
| 2 | 2.4 | 2 | 6.48 |
| 3 | 2.45 | 3 | 4.45 |
| 4 | 3.48 | 4 | 5.14 |
| 5 | 1.67 | 5 | 6.23 |
| Avg. | 2.44 | Avg. | 5.67 |
| Factor greater noise (power:no power) | | | 2.31 |

EXAMPLE 2

The system of Example 1 was used for the injection of neat methanol. Figures 17a and 17b illustrate the resulting chromatograms. FIG. 17a shows that without power no baseline disturbance occurs. FIG. 17b shows a large peak due to the electrolytic degradation of methanol with the power on.

EXAMPLE 3

The system of Example 1 was used for anion sample concentrations (all in mg/L): 0.2 $F^-$, 0.3 $Cl^-$, 1.0 $NO_.^-$, 1.5 $PO_4^{3-}$, and 1.5 $SO_4^{2-}$ with the following parameters. The chromatogram is illustrated in FIG. 5.

Separation column: Dionex Corp. AS4A-SC
Eluent: 1.8 mM Na2CO3 and 1.7 mM NaHCO3
Flow rate: 2.0 mL/min
Power setting: 4 (for regeneration) (500 mA)
Suppressor: Dionex Corp. ASRS, recycle mode

EXAMPLE 4

The system was used for cation analysis concentrations (all in mg/L): 0.5 $Li^+$, 2.0 $Na^+$, 4.0 $NH_4^+$, 2.0 $K^+$, 2.0 $Mg^{2+}$, and 10 $Ca^{2+}$ with the following parameters:

Separation Column: Dionex Corporation CS12
Eluent: 20 mM methanesulfonic acid
Flow Rate: 1.0 mL/min
Power Setting on SRC for Regeneration: Setting 4 (500 mA current)
Suppressor: Dionex Corporation CSRS (Cation Self Regenerating Suppressor), recycle mode
Regeneration Program: SRC (Self Regenerating Suppressor Controller) on for 5 min., 1 minute equilibration, data collection 12 min., SRC on at 18 min. after data collection is complete.

The chromatogram is illustrated in FIG. 6.

What is claimed is:

1. A method of anion or cation analysis by ion chromatography using periodic electrolytic chemical regeneration, said method comprising (a) chromatographically separating ionic species in a sample to be detected in a water-containing eluent solution comprising electrolyte, including transmembrane ions of opposite charge to said sample ionic species, to form a chromatography effluent, (b) flowing the chromatography effluent through a chromatography effluent flow channel of a membrane suppressor in which said chromatography effluent flow channel is separated by at least one ion exchange membrane with exchangeable ions, of the same charge as said transmembrane electrolyte ions, from at least one regenerant flow channel, (c) directing regenerant solution through said regenerant flow channel, (d) flowing the effluent containing the separated ionic species from the membrane suppressor through a detector in which the ionic species are detected, and directing this effluent to regenerant flow channels, and (e) applying an electrical potential between said chromatographic effluent flow channel and said one regenerant flow channel to assist diffusion of said transmembrane electrolyte ions through said one ion exchange membrane, said electrical potential being applied prior and after the detection of step (d) for a sufficient time to convert said electrolyte in said chromatography effluent flow channel to weakly dissociated form during suppression, wherein said electrical potential is not applied for any substantial period of time during chromatographic separation in step (a) and detection in step (d).

2. The method of claim 1 in which flow-through ion exchange means is disposed in said regenerant flow channel, said flow-through ion exchange means having ion exchange sites with exchangeable ions of the same charge as the exchangeable ions of said ion exchange membrane.

3. The method of claim 1 in which flow-through ion exchange means is disposed in said chromatography effluent flow channel, said flow-through ion exchange means having ion exchange sites with exchangeable ions of the same charge as the exchangeable ions of said ion exchange membrane.

4. The method of claim 1 in which the ionic species are anions and in step (e) water in said chromatography effluent flow channel is electrolyzed to generate hydronium ions for regeneration.

5. The method of claim 1 in which the detector effluent is the sole source of regenerant solution flowing through a detector effluent flow channel.

6. The method of claim 1 in which the ionic species are cations and in step (e) water in said chromatography effluent flow channel is electrolyzed to generate hydroxide ions for regeneration.

7. In a method of anion or cation analysis by ion chromatography by chromatographic separation of ionic species in a sample solution in an eluent comprising an electrolyte using electrolytic chemical regeneration of the suppressor by applying an electrical potential across the flow channels of a membrane suppressor, and detection of the ionic species the improvement comprising applying said electric potential for a sufficient time to regenerate said suppressor, but discontinuing application of the electrical potential during separation and detection of the anions or cations, thereby reducing background noise concomitant to said electrical potential.

8. A method of anion or cation analysis by ion chromatography using periodic electrolytic chemical regeneration of a suppressor, said method comprising (a) eluting a first sample containing ionic species to be detected in a water containing eluent solution comprising electrolyte, including transmembrane electrolyte ions of opposite charge to said first sample ionic species, through chromatographic separating means in which said first sample ionic species are separated, (b) flowing the chromatography effluent containing said first sample from said chromatographic separating means through a chromatography effluent flow channel of suppressor means in which said chromatography effluent flow channel is separated by at least one ion exchange membrane with exchangeable ions, of the same charge as said transmembrane electrolyte ions, from at least one regenerant flow channel, (c) directing regenerant solution through said one regenerant flow channel so that a portion of the transmembrane electrolyte ions from the chromatography effluent flowing through said chromatography effluent flow channel displace some of the membrane ion exchange ions, portions of said displacing ion exchange ions being retained by said ion exchange membrane, and converting said electrolyte in said chromatography effluent flow channel to weakly dissociated form, (d) flowing the treated effluent containing said first sample from said chromatography effluent flow channel through detection means in which said separated first sample ionic species are detected, (e) repeating steps (a), (b), (c) and (d) for a second sample, and (f) after step (d) and before step (e), applying an electrical potential between said chromatography effluent flow channel and said one regenerant flow channel transverse to liquid flow through said chromatography effluent flow channel to cause some of said transmembrane electrolyte ions retained by said ion exchange membrane to diffuse through said one ion exchange membrane, said one regenerant flow channel being of opposite charge to said transmembrane electrolyte ions, said electrical potential being applied for a sufficient time to regenerate the chromatography effluent flow channel capacity to effectuate, prior to step (e), the conversion of step (c) for the second sample, said electrical potential being substantially discontinued during detection in step (d) for the first and second sample, thereby reducing background noise caused by application of said electrical potential.

* * * * *